United States Patent [19]

Piotrowski et al.

[11] Patent Number: 4,904,788
[45] Date of Patent: Feb. 27, 1990

[54] HYDROCARBON-SOLUBLE COMPLEXES OF MAGNESIUM ALKOXIDES WITH MAGNESIUM AMIDES

[75] Inventors: Andrzej M. Piotrowski, Thornwood, N.Y.; Dennis B. Malpass, LaPorte, Tex.

[73] Assignee: Texas Alkyls, Inc., Deer Park, Tex.

[21] Appl. No.: 203,192

[22] Filed: Jun. 7, 1988

[51] Int. Cl.$^4$ ................................................ C07F 3/02
[52] U.S. Cl. ................................... 546/248; 564/443; 564/503; 564/508
[58] Field of Search ................ 546/248; 564/508, 503, 564/443

[56] References Cited

U.S. PATENT DOCUMENTS 4,178,300 12/1979 Van Den Berg .................... 260/413
4,634,786 1/1987 Kamienski ........................... 556/187

OTHER PUBLICATIONS

*The Condensed Chemical Dictionary,* 9th Ed., Van Nostrand Reinhold, New York, 1977, p. 39.

*Primary Examiner*—Richard A. Schwartz
*Attorney, Agent, or Firm*—Richard P. Fennelly; Louis A. Morris

[57] ABSTRACT

Hydrocarbon-soluble complexes of magnesium alkoxides with magnesium amides are described. The magnesium amide moiety is derived from an amine (e.g., an N-heterocyclic amine). The complexes can be formed by reaction between a magnesium alkyl and a mixture of aliphatic alcohols and an amine.

3 Claims, No Drawings

HYDROCARBON-SOLUBLE COMPLEXES OF MAGNESIUM ALKOXIDES WITH MAGNESIUM AMIDES

BACKGROUND OF THE INVENTION

1. Field of the Invention

The current invention relates to hydrocarbon-soluble complexes of magnesium alkoxides with magnesium amides.

2. Description of the Prior Art

Recent interest has focused upon deriving hydrocarbon-soluble magnesium alkoxides which can function, for example, as catalyst precursors.

U.S. Pat. No. 4,178,300 to van den Berg mentions that solutions of organooxy magnesium compounds of desirably low viscosity can be prepared by dissolving a magnesium compound of that type in the presence of an organooxy compound of a transition metal from Groups IV through VI of the Periodic Table. Representative transition metal compounds include those of titanium, zirconium, vanadium, and chromium. Preferred transition metal compounds are those of titanium.

More recently, U.S. Pat. No. 4,634,786 of C. W. Kamienski indicates that magnesium primary dialkoxides having 2-alkyl substituents in the alcohol moiety posses good solubility, especially in the presence of minor amounts of aluminum alkoxides and lithium or potassium alkoxides derived from the same alcohol moiety.

SUMMARY OF THE PRESENT INVENTION

It has now been found that it is possible to solubilize magnesium alkoxides by forming hydrocarbonsoluble complexes of magnesium alkoxides with magnesium amides. For example, such complexes can be formed by utilizing ligands on a magnesium atom derived from aliphatic alcohols (or mixtures thereof) in conjunction with an amine.

DETAILED DESCRIPTION OF THE PRESENT INVENTION

The hydrocarbon soluble complexes of magnesium alkoxides with magnesium amides that are contemplated by the present invention are or can be easily formed by conducting a reaction between a magnesium alkyl and the desired mixture of aliphatic alcohols and amine in an appropriate solvent. Since heating of the mixture of such components facilitates the desired reaction, solvents which boil above about 90° C. (e.g., heptane or toluene) are most suitable. Such a reaction insures that the resulting composition is a complex of magnesium alkoxides and magnesium amide having the formula $Mg(OR)_x(NR'R'')_y$ where R is either straight or branched alkyl such as n-butyl, 2-ethyl-1-hexyl, n-decyl, and so forth. The moieties R' and R'' are derived from an amine which can be aliphatic or cyclic (e.g., and N-heterocyclic compound). The amine is represented by the formula HNR'R'' where R' and R'' can independently be hydrogen, aryl, and/or alkyl. If desired, N can be part of a heterocyclic ring, in which case R' and R'' are conjoint. If R' and R'' are conjoint in the form of an N-heterocyclic ring, such a compound can have the structure

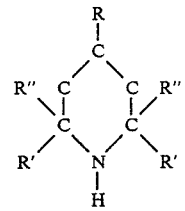

where R can be hydrogen, alkyl or aryl, and R' and R'' can independently be alkyl and/or aryl. A representative example of such an amine is 2,2,6,6-tetramethylpiperidine. Generally speaking, the individual values for x and y can range anywhere from about 0.1 to about 1.9 with the sum of x and y being substantially equal to 2.

The foregoing invention is further illustrated by the Examples which follow.

COMPARATIVE EXAMPLE A

To 320 grams of a 15% solution of n-butylethyl-magnesium (BEM) (38.1 grams or 0.526 mole) in heptane cooled in an oil bath, a mixture of n-butanol (37 grams of 0.50 mole) and 2-ethyl-1-hexanol (32.5 grams of 0.25 mole) was added slowly. Temperature of the oil bath and rate of addition were adjusted to warm reaction mixture to 65° C. at the end of the addition. Some solids were formed during the reaction but were redissolved upon stirring for about 15 minutes at 65° C. The solution formed was clear and colorless but somewhat viscous. It was cooled and stored overnight at ambient temperature. Viscosity of the solution increased overnight such that the material was no longer transferable.

COMPARATIVE EXAMPLE B

To 64.1 grams of a 22% solution of BEM (0.128 mole) in heptane, a mixture of 6.9 grams of n-butanol (0.093 mole) and 21.8 grams of 2-ethyl-1-hexanol (0.167 mole) was added. After the addition was completed, the pot was heated to reflux (approximately 95° C.) for one hour. A clear, colorless, very viscous (even at 95° C.) solution was formed which turned into a glass at room temperature.

EXAMPLE 1

To 53.1 grams (0.106 mole) of BEM solution in heptane there was slowly added a mixture of 1-butanol (7.3 grams, 0.098 mole) and 2-ethyl-1-hexanol (8.5 grams, 0.065 mole). At the end of the addition, the reaction mixture was heated to reflux (approximately 95° C.) for one hour. The pot was then cooled and 7.6 grams of 2,2,6,6-tetramethylpiperidine (TMP) (0.054 mole) were added over a period of 15 minutes. The reaction mixture was then refluxed for one hour. A yellow mobile solution was obtained.

| ANALYSIS AND PHYSICAL PROPERTIES OF PRODUCTS | | | |
|---|---|---|---|
| Example | Mg Wt. % | Viscosity (Centipoise at 25° C.) | Density (g/ml at 25° C.) |
| A | 3.00 | >>1000 | — |
| B | — | glass | — |
| 1 | 3.89 | 21 | 0.777 |

The foregoing Examples represent certain preferred embodiments of the present invention and should not, therefore, be construed in a limiting sense. The scope of protection that is sought is set forth in the claims which follow.

We claim:

1. A hydrocarbon-soluble complex of a magnesium alkoxide and a magnesium amide of the formula $Mg(OR)_x(NR'R'')_y$, where R is alkyl, R' and R'' are selected from the group consisting of hydrogen, aryl, alkyl, and, as conjoint, part of a heterocyclic ring, and x and y can range from 0.1 to 1.9 with their sum being 2.

2. A complex as claimed in claim 1 wherein the moiety NR'R'' is from an N-heterocyclic amine.

3. A hydrocarbon-soluble complex of the formula $Mg(OR)_x(NR'R'')_y$, where R is selected from the group consisting of butyl and 2-ethyl-1-hexyl, wherein the moiety NR'R'' is from 2,2,6,6-tetramethylpiperidine, and x and y can range from 0.1 to 1.9 with their sum being 2.

* * * * *